United States Patent
Virkki et al.

[11] Patent Number: 5,948,454
[45] Date of Patent: Sep. 7, 1999

[54] METHOD FOR TREATMENT OF FIBROUS CROPS WITH A MODIFIED CELLULASE TO IMPROVE FEED VALUES STORAGE AND OTHER PROPERTIES

[75] Inventors: Markku Virkki, Espoo; Juha Apajalahti, Helsinki; Kalevi Visuri, Kantvik, all of Finland

[73] Assignee: SSV Development OY, Helsinki, Finland

[21] Appl. No.: 08/279,451

[22] Filed: Jul. 22, 1994

Related U.S. Application Data

[63] Continuation of application No. 07/867,039, Apr. 10, 1992, abandoned.

[51] Int. Cl.⁶ ........................................................ A23B 7/10
[52] U.S. Cl. ............................... 426/53; 426/49; 426/52; 426/54; 426/623; 426/630
[58] Field of Search .................... 426/53, 54, 2, 426/49, 52, 615, 630, 623

[56] References Cited

U.S. PATENT DOCUMENTS 5,053,233  10/1991  Setälä et al. ................................ 426/53

FOREIGN PATENT DOCUMENTS

| | | |
|---|---|---|
| 0 113 626 | 7/1984 | European Pat. Off. . |
| 296406 | 12/1991 | Germany ................................. 426/53 |
| 52-34546 | 9/1977 | Japan ...................................... 426/53 |
| 4117244 | 4/1992 | Japan ...................................... 426/53 |
| 2046 567 | 11/1980 | United Kingdom . |
| 91/05039 | 4/1991 | WIPO . |
| 9115966 | 10/1991 | WIPO .................................... 426/53 |
| 91/18090 | 11/1991 | WIPO . |
| PCT/WO10945 | 7/1992 | WIPO . |

OTHER PUBLICATIONS

Molecular Microbiology, 3225–3235 (Jul. '92) 6(21).

Enzyme Microb. Technol., 227–233 (Mar. '91) vol. 13.

Beldman, et al., The Cellulase of *Trichoderma viride*, 301–308, (1985).

*Primary Examiner*—Leslie Wong
*Attorney, Agent, or Firm*—Kenyon & Kenyon

[57] ABSTRACT

The subject invention is directed to enzymatic methods for improving the conservation (storage) and feed values of fibrous crops by treating the crops with a cellulase enzyme mixture.

19 Claims, 4 Drawing Sheets

METHOD FOR TREATMENT OF FIBROUS CROPS WITH A MODIFIED CELLULASE TO IMPROVE FEED VALUES STORAGE AND OTHER PROPERTIES

This application is a continuation of application Ser. No. 07/867,039, filed on Apr. 10, 1992 now abandoned.

TECHNICAL FIELD

This invention relates to improvement, through treatment with novel enzyme preparations, in the feed value of fibrous crops for use by ruminant and monogastric animals. More particularly, the invention relates to the fractionation of cellulase enzymes derived, for example, but not in particular, from Trichoderma species, to increase their effectiveness in improving the availability of the energy from cellulose and hemicellulose units of fiber to the microbes in the rumen of ruminant species and/or the digestive processes of monogastric and ruminants—monogastric animals do not have enzyme systems capable of utilizing fiber. Further, these novel enzyme products can be used to treat fibrous crops during conservation with beneficial effects on the ensilage process as well as the treatment of conserved crops just prior to feeding to the animal crops. The invention also relates to methods for the preparation of said enzyme products.

BACKGROUND OF THE INVENTION

As fibrous crops mature the yield of energy per unit of land area increases, but the availability of energy, i.e. cellulose and hemicellulose decreases because of the process of plant lignification in which the cellulose chains in the plant cell walls become lignified through complex cross linkages. This results in a considerable reduction in the digestibility of the dry matter components to the animal. Thus, whilst from an economic viewpoint, the crop should be harvested mature, at peak dry matter yield, the limitation on digestibility of energy forces harvest to take place at a more immature stage with a lower dry matter yield and potential problems with conservation due to lower dry matter content. By breaking such cross links between cellulose units, enzymes can allow crops to be harvested at later maturities, thus increasing energy yield without the usual reduction in digestibility. Also, the same process can make sugars available to silage microbes, thus improving the conservation of such crops under adverse weather conditions where dry matter content is low.

Conservation

The preservation of fibrous crops (grass, legumes, whole crop cereals—maize, sorghum, etc.) for future use as animal feed basically relies on either the removal of water by drying (hay etc.) or the exclusion of air and acidification of the mass to a point where the activities of epiphytic spoilage microorganisms (yeasts, moulds and bacteria) are controlled and the enzyme activities of the plant material are restricted. In practice, a pH of less than about 4.2 is needed, this can be acheived either through the addition of acid to the crop or by means of acids produced through fermentation by epiphytic microorganisms.

Current environment concerns make the addition of acid less acceptable. The environmental concerns are amplified by the generally used acids such as formic acid. These acids increase the production of acidic effluent from wet crops.

The alternative is to rely on natural fermentation. However, natural fermentation produces variable results which are sometimes insufficient. For example, undesirable epiphytes may dominate the desirable lactic acid bacteria in crops that contain small amounts of sugar substrates. The desirable lactic acid bacteria, i.e. homolactic bacteria, produce mainly lactic acid. This lactic acid production lowers the pH without significant damage to the feed value, especially protein quality. In contrast, when undesirable epiphytes dominate, the pH is only slowly reduced and it may not reach a sufficiently low value. The resulting effect on feed quality is then detrimental to animal performance.

The situation can be improved by adding the desirable lactic acid bacteria to the crop at levels sufficient to dominate the epiphytes. But this technique does not help where the sugar level in the crop is low. The water soluble carbohydrates required by the lactic acid bacteria may be added to the crop. For example, one could add molasses, starch or sugars such as glucose, lactose and sucrose. However, this approach creates other problems. Generally, a large amount of sugar must be added, i.e. 10–20 kilograms sugar/tonne and between 35 to 45 kilograms molasses/tonne crop. It is difficult to apply such high quantities of these viscous materials to the crop. It is also difficult to evenly add dry materials to the crop. Some additives, such as glucose, lactose and sucrose, are too expensive to use. Moreover, lactic acid bacteria do not use starch effectively unless amylase is present to convert the starch to sugar.

Alternatively, enzymes can be used to break the complex structural carbohydrates in the crops into simple sugars. Lactic acid bacteria can use the sugars released this way and dominate fermentation. U.S. Pat. No. 4,751,089, to Heikonen et al., recites a method for ensiling fodder and grain by adding glucose oxidase. The glucose oxidase produces gluconic acid from glucose in the soluble carbohydrates. The gluconic acid accumulation decrease the pH. According to said U.S. patent other enzymes, such as cellulase, hemicellulase and B-glucosidase can be added to increase the glucose production.

The use of cellulolytic enzymes to preserve and enhance the nutritive value of forage for silage and to improve the palatability, digestibility and rate of digestion of treated forage by ruminants has also been described in U.S. Ser. No. 510,506, filed on Apr. 18, 1990, now abandoned. The enzyme composition disclosed in that application preferably contains at least one enzyme from the group consisting of pectinase, cellulase, xylanase, amylase, arabinosidase, cutinase, lipase and esterase and may be used in combination with homolactic bacteria.

However, cellulolytic enzymes can produce undesirable side effects when added to fibrous crops having little (i.e. less than 25%) dry matter such as immature crops. For example, cellulolytic enzymes can increase the amount and pattern of effluent flow. The effluent flow comprises soluble cellular materials. These materials give the effluent a high BOD and can cause environmental problems. Also, the effluent loss reduces the feed value of the crop. These enzymes can also increase the lactic acid values and change fiber structure to a degree that reduces animal performance. Moreover, as a result of the increased sugar levels produced by the enzymes, yeasts and moulds may grow better. Increased yeast and mould growth may lower the aerobic stability and produce harmful mycotoxins.

Feed Efficiency

In ruminants the efficiency with which fiber is used by the host animal depends on the effective actions of a mixed rumen microbial population. The composition of this microbial population depends upon the feed. The end result of microbial activity on energy sources is the production of volatile fatty acids which act as precursors within the tissue of the host for the supply of energy for metabolic processes and for the synthesis of animal products e.g. milk, meat and wool. The efficiency with which these products are produced depends on the relative proportions of the volatile fatty acids, especially acetic, propionic and butyric. Feeds with a high starch and/or sugar content promote the synthesis of butyric and propionic acid whereas fiber promotes acetic acid. The desirable type of rumen fermentation depends upon the animal product required. Thus, the ability to modify the substrate is of prime economic importance, especially the ability to modify the reactivity of fiber in this respect, since this is the lowest cost form of energy.

For monogastric animals, fiber is not a ready source of energy but it is present in most sources of starch, e.g. grains. Fiber is also of importance in maintaining the normal gut function. This is associated with the reactivity of the fiber, e.g. cation exchange capacity. The ability to release energy from the fiber fraction of the diet and to improve its reactivity is thus of great importance in monogastric nutrition and health.

Enzyme products for the preservation of low dry matter forage and the enhancement of feed utilization present two major problems. Firstly, in an efficient ensilage process, the enzyme should produce the desired pH, lactic acid and carbohydrate concentration while minimizing the effluent production.

The treatment of forage with a complete mixture of cellulolytic enzymes decreases the fiber content of the silage by solubilizing polymeric carbohydrates. Over effective digestion results in total cell wall collapse and consequently in production of effluent with high sugar content. Fermentation during ensilage is stimulated, lactic acid accumulates and pH drops. Under these conditions bacteria are inhibited but the enzymes keep producing monomeric carbohydrates, part of which may be lost with the effluent. The silage containing high concentrations of lactic acid and easily fermentable sugars may be harmful to the ruminant, causing lactic acidosis and digestive disorders.

Secondly, in order to ensure efficient rumen function and feed utilization by ruminants, the amount of sugar available to the rumen microbes and the reactivity of the fiber should be optimized.

The object of this invention is to provide an enzyme preparation for different crops, maturities and dry matter content which does not have the disadvantages of the known preparations. More particularly, the object of this invention is to provide enzyme combinations which; give beneficial changes in the structure of plant cells walls; provide only the needed amount of sugars for an effective silage; not increase the production of effluent; not encourage yeast or mould growth; but which are able to change the structure of the plant polymers so that they are more susceptible to further enzymatic hydrolysis in the rumen and have improved digestion in the monogastic digestive tract.

A further object of this invention is to provide methods for the preparation of said enzyme products.

SUMMARY OF THE INVENTION

It has now surprisingly been found that the adverse effects of the commercial products are caused by the presence of certain enzyme combinations in the commercial grade cellulases used in said products. By the fractionation of said commercial enzymes in accordance with this invention novel enzyme products have been obtained, each containing several individual enzymes and having its own characteristic features on the basis of which the most suitable fractions for each particular use can be selected.

Separation methods useful in the practice of the present invention include those methods that separate commercial cellulase compositions on the basis of ion exchange properties of the proteins. For example, chromatographic methods are useful, such as ion exchange chromatography. Useful resins include Q-Sepharose and Mono-Q (both from Pharmacia).

The cellulase fractions, in various combinations, are useful in preserving fibrous crops and improving feed utilization by ruminants and monogastric animals. Each cellulase fraction has a characteristic set of enzymes and hence distinct effects on the fiber crop, during ensiling as well as in the rumen and small intestine after the feed intake. The fractions can be used alone, or in combinations, and/or with suitable beneficial microorganisms, like bacteria or yeast, to produce different effects in each particular application. The products can also be used on conserved feeds just prior to feeding.

DETAILED DESCRIPTION OF THE INVENTION

Commercial grade cellulolytic enzyme mixtures (such as those sold under the trade names Cytolase-123 from Genencor, sometimes referred to here as Cytolase typically contain large numbers of enzymes. Commercially important cellulolytic enzyme mixtures are, e.g., those derived from Trichoderma species, for example *Trichoderma longibrachiatum*. Other cellulolytic enzyme mixtures such as those from bacterial or other fungal sources have similar properties.

The effect of the enzyme fractions, both alone and in several different combinations, on treated forage and silage and on animal performance have been determined by measuring a large number of parameters. The most important parameters as regards animal performance are the amount and types of sugar released and the changes in the structure of the fiber, which control the rumen fermentation process and digestion in the monogastric tract. By measuring the potential of the fiber to release sugars before and after the ensilage process the loss in feed value during preservation can be determined. If a substantial part of the structural carbohydrate is converted to acid during the ensilage process, the conservation is good. On the other hand, this reduces the energy available to the rumen microbes and thus limits the feed value. An optimal combination would be a product that releases sufficient sugar to ensure a good ensilage and still improve rumen activity. An important characteristic is also the potential for effluent production, which is connected with the sugar release activity.

Each of the obtained enzyme fractions contains a characteristic set of individual enzymes and has distinct effects on the fiber structure, sugar release, silage conservation and effluent production.

On the basis of said features it is possible to choose the most suitable fraction for each particular use. To conserve the crops, fractions that produce a pH of about 4.0 within 48 hours and a level of residual sugar that keeps the lactobacillae homolactic should be used. Selected fractions can also be used to improve the feed value of the fresh or conserved fibrous crop prior to feeding. The effluent problem can be overcome by avoiding those fractions which cause too effective sugar release.

More particularly, for the ensiling of low dry matter fibrous crops, enzyme fractions B or C, alone or in combination would be a preferred choice since they supply adequate levels of sugar to promote a beneficial silage fermentation without increasing effluent flow. Fraction A, whilst giving a small increase in effluent flow, increases the number of free ends of sugar chains and makes the fiber susceptible to further enzymatic hydrolysis by rumen microorganisms and in the monogastric digestive process. Fraction A, alone or in combination with B, C, or B and C improves the availability of sugar to the rumen microbes. Fraction A also improves the reactivity of the fiber both alone and in combination with B, C, and B and C. Thus, whilst fractions B, C or BC are preferred for the conservation of low dry matter crops without effluent effects, the further addition of fraction A improves the reactivity of the fiber and feed value.

Where effluent is not a problem, e.g. fibrous crops ensiled at dry matter levels above 25%, fraction A, alone and in combinations with B, C and, B and C, can be used to improve both preservation and animal performance. These combinations can also be used to improve the feed value and stability of fresh or conserved fibrous crops treated prior to feeding.

In low dry matter crops, the effluent problem can be overcome by deleting or avoiding fractions A and D. Fraction D is mainly responsible for the adverse pattern of effluent flow. Fraction D has also adverse effects on the sugar release in converting too much complex carbohydrate to sugar. Further, fraction D strongly reduces the activity of the fiber.

When it is desirable to achieve a rapid improvement in sugar release, for instance prior to feeding the animal, fraction D and combinations thereof are preferred for treating fibrous crops for use by ruminant and especially monogastric animals.

The enzyme products of this invention hence offer several advantages. By the use of appropriate enzyme fractions, alone or in suitable combinations, (with or without exogenous beneficial microorganisms) major improvements are achieved with respect both to the preservation of fibrous crop and the utilization of the feed and the animal performance. Four points deserve to be especially emphasized: crop conservation is improved, the effluent problem can be solved, the sugar release value can be improved and the fiber reactivity value can be improved by the use of the enzyme products of this invention.

EXAMPLE 1

FRACTIONATION OF CYTOLASE-123

Figure 1:
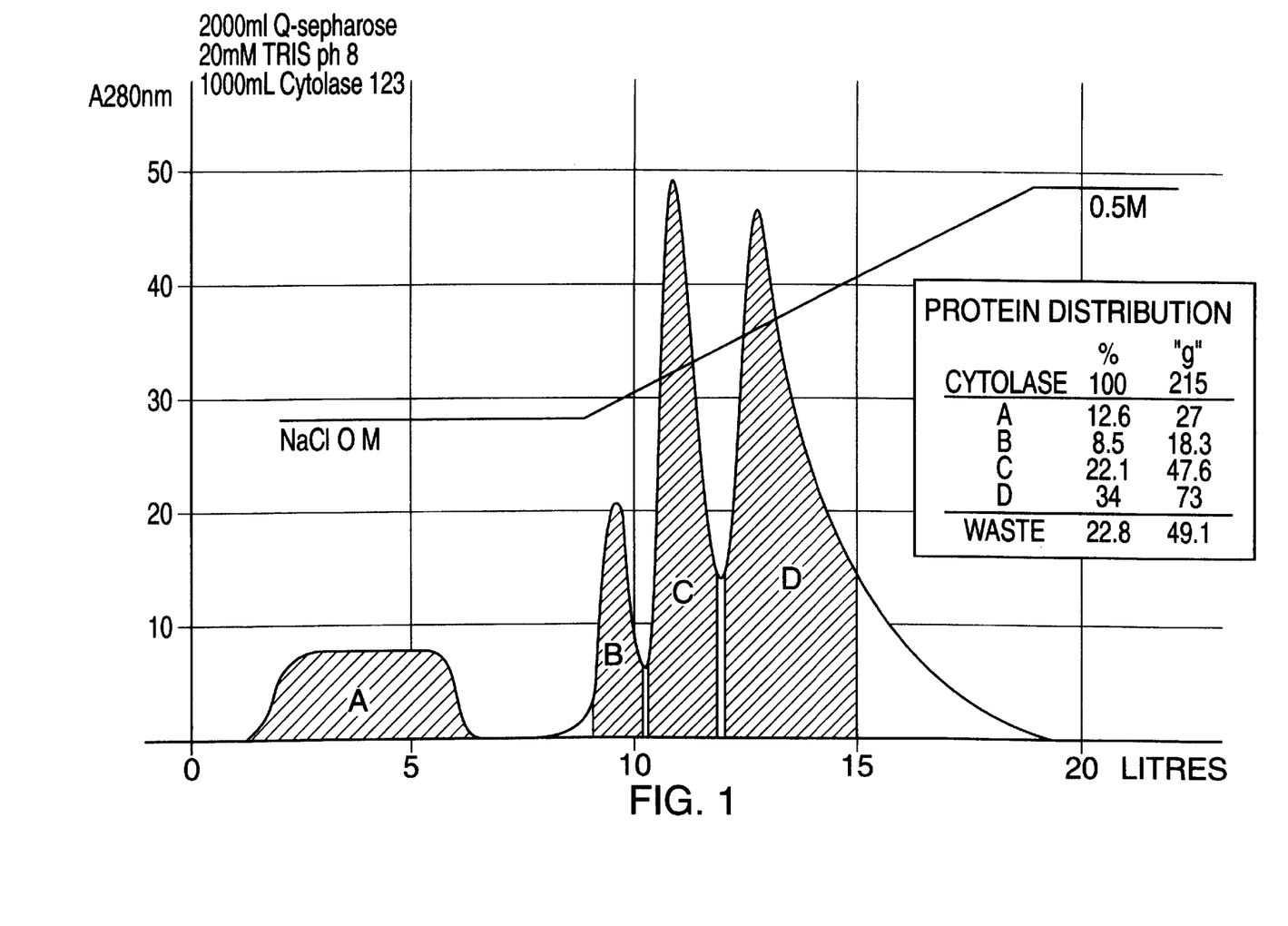
FIG. 1 shows the absorbance at 280 nm of the eluate from a separation of a commercial cellulase on an anion exchange column.
Figure 2:
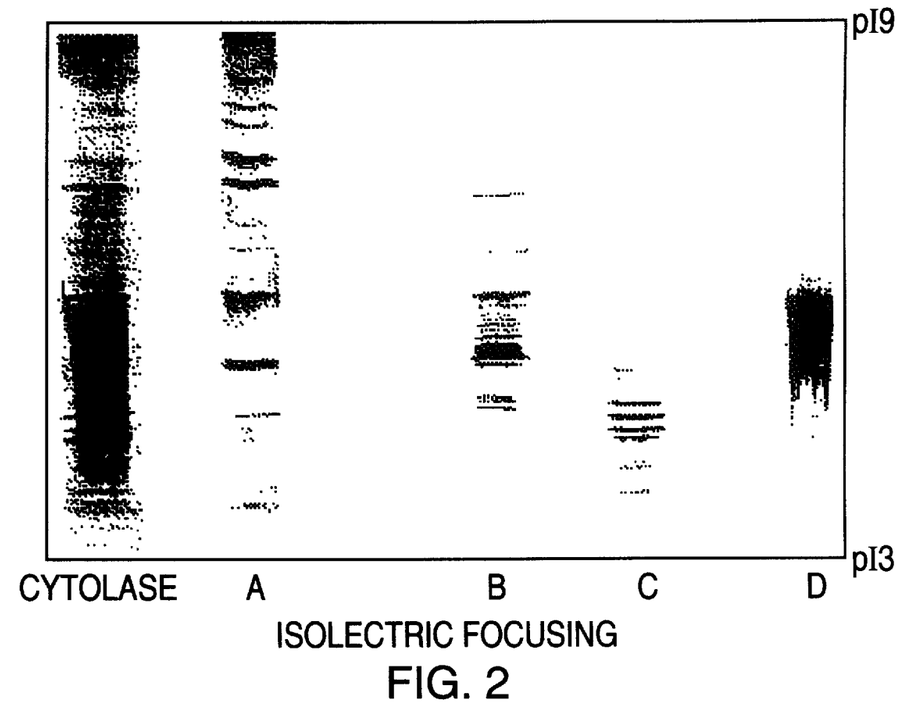
FIG. 2 shows the isolectric points of proteins in a commercial cellulase and each of its four major fractions as a result of anion exchange chromatography.

Fractionation was made in a 2 liter column of Pharmacia Q-Sepharose anion exchanger. For each run, 1 liter of Cytolase-123 (Genencor) containing about 200 g protein (based on the absorbance at 280 nm) at pH 5.2 was adjusted to pH 8 and to the conductivity of the 20 mM tris-buffer by ultrafiltration followed by dilution with water. The adjusted enzyme solution was fed into the column. The unabsorbed material (fraction A) was washed out with about 10 liters of the 20 mM tris-buffer. The absorbed enzymes were eluted with a linear gradient of 0–0.5 M NaCl having a total volume of about 10 liters. The column eluate was collected. The bound fractions were eluted with 20 mM tris buffer at sodium chloride concentrations of 80mM (Fraction B), 150 mM (Fraction C) and 500 mM for Fraction D. (Hereinafter, these fractions are referred to as fractions A, B, C and D in order of elution.) The fractionation results are shown graphically in FIG. 1.

Fractions A, B, C and D had the following amounts of protein, based on absorbance at 280 nm:

A 27 g

B 18.3 g

C 47.6 g

D 73 g.

It is believed that the tail of fraction D (i.e. the eluate in the 0.3 M NaCl and greater buffer) only contained traces of protein material and the absorbance observed in the tail was due to some small molecular weight UV absorbing material.

Figure 3:
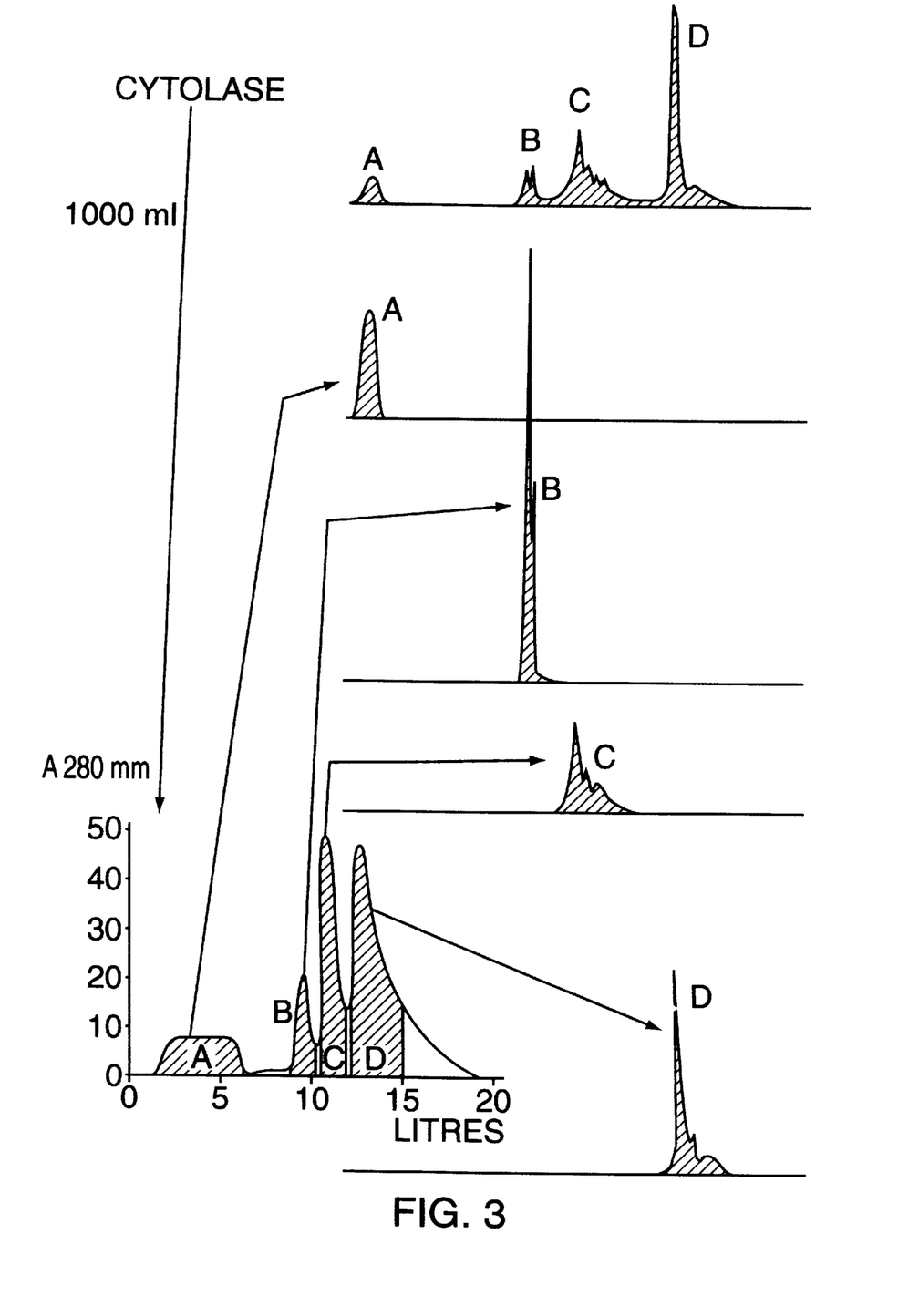
FIG. 3 shows the absorbance at 280 nm of the eluate from separations of a commercial cellulase and its four major anion exchange fractions (Fractions A–D) on a Mono Q analytical anion exchange column.

The fractions were analyzed with isoelectric focusing in gels to separate proteins between isoelectric points of 3 to 9. These results were used as fingerprints to compare fractions coming from different separation processes. The results obtained are shown graphically in FIG. 1. The most important fractions were also analyzed by analytical liquid chromatography on Mono-Q or on a cation exchange column, which have excellent resolving power for proteins. The results are shown graphically in FIG. 3.

Figure 4:
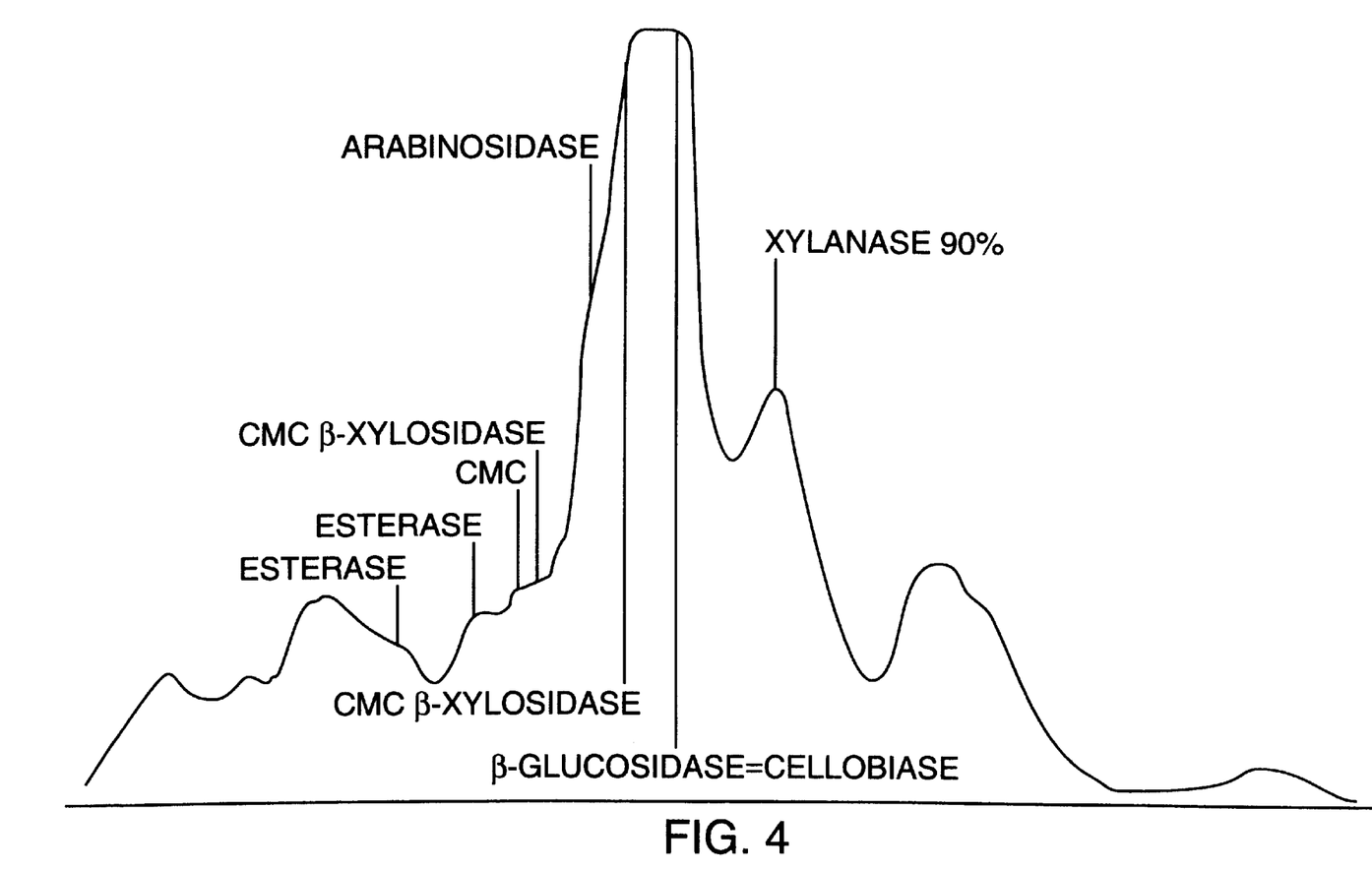
FIG. 4 shows the absorbance at 280 nm of the eluate from a separation of commercial cellulase fraction A on a cation exchange column of CM-Sepharose (Pharmacia).

The material which was unabsorbed on Q-sepharose (fraction A), was fractionated with a cation exchange CM-Sepharose column. These results are shown in FIG. 4. Cytolase was divided with Q-Sepharose into 4 enzyme fractions, each of which contain several different proteins and enzymes. The distribution of various activities in Cytolase and the 4 fractions is described in table 1. The results show that Cytolase-123 is a very complex enzyme mixture and that even the obtained fractions are multienzyme preparations. The fractions can be further purified e.g. chromatographically or by precipitation, if desired.

Alternatively the enzymes can be eluted using differing combinations of pH, concentrations of salt, and concentration and type of buffers. For example, using 20 mM tris buffer at pH 7.6 resulted in the more loose binding of fractions B, C, and D to the column, such that they were eluted at salt concentrations of 20 mM (Fraction B), 115 mM (Fraction C) and 500 mM for Fraction D. However, changes to these parameters does not change the order in which the fractions elute from the column after fraction A had been washed through. In an alternative procedure, the enzymes can be eluted with a stepwise gradient of similar pH, buffer and salt concentrations.

Unfractionated Cytolase and fractions A, B, C and D were analyzed with analytical liquid chromatography using a Mono-Q column (Pharmacia). The results show that fractions B, C and D each contain more than one component. See FIG. 3.

Cellobiohydrolase I, Cellobiohydrolase II and Endogluconase I were identified through the use of anti-Cellobiohydrolase I, anti-Cellobiohydrolase II and anti-Endogluconase I antisera. (See Table 1).

The material that was not absorbed on Q-sepharose (fraction A), was fractionated with a cation CM-Sepharose column. The CM-Sepharose fractionation of the Q-Sepharose fraction A revealed, based on enzyme activity assays, that the material that eluted at points 4.1 and 4.2 had Esterase activity; the material that eluted at points 4.3, 4.4 and 4.5 had CMC activity; the material that eluted at points 4.4 and 4.5 also had β-Xylosidase activity; the material that eluted at about point 4.4 had Arabinosidase activity as well; the material that eluted at point 4.6 had β-glucosidase (cellobiose) activity; and the material that eluted at point 4.7 had Xylanase activity.

TABLE 1

Enzyme Activities*
for Cytolase and the Fractions

|  | FPU | CMC | Cello-biase | Xyla-nase | Arabi-nosidase | Xylosi-dase | Ester-ase |
|---|---|---|---|---|---|---|---|
| CYTO-LASE | 81.2 | 5231 | 71 | 1559 | 8.6 | 2.4 | 0.26 |
| A*** | 9.6 | 285 | 64 | 780 | 7.5 | 0.4 | 0.03 |
| B*** CBH II** | 1.7 | 15 | 0.1 | 2 | 0 | 0 | 0.06 |
| C*** EG I** | 4.4 | 633 | 0.7 | 181 | 0 | 0.9 | 0.03 |
| D*** CBH I** | 9.3 | 121 | 0.1 | 28 | 0 | 0.2 | 0.05 |

*FPU = Filter Paper Units - liberates 1 micromole reducing sugars from 50 mg of Whatman No 1 filter paper in one minute at 50° C. at pH 4.8 in reaction volume of 2 ml.
CMC = Carboxy Methyl Cellulose units - liberates 1 micromole reducing sugars from 10 mg of carboxy methyl cellulose in 1 minute at 50° C. at pH 4.8 in reaction volume of 2 ml.
Cellobiase Unit - liberates 1 nanomole glucose per second from 1.8 micromoles of 4-nitrophenyl - Beta-glucopyranoside at 50° C. at pH 4.8 in reaction volume of 2 ml.
Xylanase Unit - liberates 1 micromole reducing sugars from 10 mg of xylan in 1 minute at 50° C. at pH 4.2 in reaction volume of 2 ml.
Arabinosidase Unit - liberates 1 nanomole p-nitrophenol per second from 3.6 micromoles of p-nitrophenyl-alpha-L-arabinofuranoside at 50° C. at pH 4.0 in reaction volume of 2 ml.
Xylosidase Unit - liberates 1 nanomole p-nitrophenol per second from 3.6 micromoles of p-nitrophenyl-Beta-D-xylopyranoside at 40° C. at pH 5 in reaction volume of 2 ml.
Esterase Unit - liberates 1 nanomole p-nitrophenol per second from 1.8 micromoles of p-nitrophenyl acetate at 50° C. at pH 4.8 in reaction volume of 2 ml.
**CBH I is Cellobiohydrolase I, CBH II is Cellobiohydrolase II, and EG I is Endoglucanase I as identified with antisera.
***The fractions A, B, C and D were tested at their proportional concentration in the original Cytolase

EXAMPLE 2

Effect of Enzyme Fractions Prepared From Cytolase-123 on the Fiber Structure and Chemical Composition of Silage Tetraploid ryegrass (fertilization 120 kg N/hectare) was cut by hand using aseptic techniques, transported cold and the experiment started within 5 hours of cutting. The dry matter content was 13% wt/wt. The grass was cut with scissors to 1 cm pieces and placed in plastic bags, each containing 80 g of fresh grass. Replicate samples were treated with all combinations of Cytolase-123 fractions A, B, C and D. After the enzyme treatment the grass was packed in 25 g aliquots into 160 ml serum bottles, flushed with anaerobic gas for 5 minutes and sealed with butyl rubber stoppers. The bottles were incubated at 30° C. for 6 weeks and then the neutral detergent fiber (NDF) extracted:

75 ml of water was added to the bottles with treated grass, shaken for 1 hour at room temperature and filtered through a glass sinter. The filtrate was used for various analyses and the precipitate extracted further. Neutral detergent extraction of the precipitate was carried out as follows: i) the precipitate was quantitatively suspended in 100 ml of a solution (pH 7) containing per liter 19.6 g of Titriplex 111, 3.6 g of $Na_2B_4O_7$, 4.6 g of $Na_2HPO_4$, 30 g of sodiumdodecylsulphate and 10 ml of ethylenglycolmonoethylether and agitated for 40 min at 60° C.; ii) the temperature of the extraction was rapidly raised to 75° C. and filtered hot using a glass sinter; iii) the precipitate was then washed with 100 ml of water by shaking for 15 min at 60° C., temperature raised rapidly to 75° C. and the suspension filtered; this water extraction was repeated; iv) the precipitate was then extracted with 100 ml of a salt solution containing per liter 3.64 g of $KNO_3$, 1.76 g of KCl, 0.17 g of $NaNO_3$, 1.92 g of $Ca(NO_3)_2 \cdot 4H_2O$ and 1.96 g of $Mg(NO_3)_2 \cdot 6H_2O$; v) when the temperature had declined from 60 to 40° C., the suspension was filtered vi) water extraction (item iii) was repeated twice; vii) the precipitate was extracted with 75 ml of acetone for 15 min and filtered; this was repeated 4 times; and viii) the NDF obtained was dried on a vacuum connected glass sinter overnight.

1. Effects of the Enzyme Fractions on Composition of Soluble Silage Constituents D- and L-lactic acids were analyzed using the Boehringer & Mannheim GmbH enzymatic assay kit and a procedure suggested by the manufacturer. Ammonium was analyzed from the alkalized samples using an ammonia specific electrode.

Soluble protein was analyzed by the method of Lowry. Soluble sugars were analyzed as trimethylsilyl derivatives by GLC using a capillary column and a temperature program. An internal standard method with two internal standards (erythritol and phenyl-B-D-glycopyranoside) was used.

The results obtained are summarized in table 2.

TABLE 2

Effects of enzyme fractions, alone and in different combinations, on the composition of soluble silage constituents.

| Enzyme | Residual sugar in silo mg/g (DW) | Ammonium umol/g (DM) | Soluble Protein mg/g (DM) | Lactic acid D as % D + L |
|---|---|---|---|---|
| Zero | 0 | 140 | 50 | 46 |
| ABCD | 20 | 119 | 49 | 48 |
| ABC | 5 | 110 | 58 | 51 |
| ABD | 21 | 119 | 60 | 54 |
| ACD | 15 | 156 | 58 | 51 |
| BCD | 44 | 151 | 57 | 45 |
| AB | -7 | 154 | 54 | 48 |
| AC | 2 | 172 | 53 | 48 |
| AD | 22 | 186 | 57 | 50 |
| BC | 22 | 174 | 58 | 46 |
| BD | 45 | 147 | 54 | 55 |
| CD | 13 | 151 | 57 | 47 |
| A | 2 | 149 | 64 | 46 |
| B | -2 | 172 | 52 | 49 |
| C | 0 | 177 | 51 | 48 |
| D | 52 | 179 | 51 | 46 |

The residual sugar values are stated relative to the value for the untreated control, positive values show an increased concentration and negative values a decrease. Monosaccharides and disaccharides were analysed and their totals presented as the residual sugar values. The residual sugar values may not reflect total sugar release in the silo due to possible differences in uptake and/or growth of the silage micro-organisms.

All silages were well preserved, having a pH value of about 4 or lower and a high concentration of lactic acid. With respect to the form of lactic acid, it can be mentioned that the enzyme treatment did not significantly affect the ratio of the two forms of lactate. In all cases, about 50% of the lactate was in D form.

The amount of residual sugar by combinations of fractions ABD, BCD, AD, BC, BD and D is greater than that of all fractions combined, ABCD. The choice of enzyme fractions had a clear effect on the residual concentration of glucose, xylose, fructose and arabinose. The concentration of each of them correlated with the others; the treatment showing highest glucose concentration also giving the highest concentrations for the other sugars etc. Fraction D was the most powerful apparent sugar producer in silage. Fraction B and the combination AB showed negative values in apparent sugar production.

The concentration of soluble protein was between 50 and 60 mg/g of dry grass in all treatments; the silage quality was hence not reduced by the enzyme treatment. Ammonium levels, likewise, did not correlate with the presence of any enzyme fractions.

2. Effect of the Enzyme Fractions on Fiber Structure Analysis of the NDF Structure.

The NDF obtained was weighed and expressed as a percentage of the dry matter of the starting material.

Susceptibility to enzymatic hydrolysis was determined by hydrolyzing NDF with a complete cellulolytic enzyme mixture Cytolase-123 (50.000 HEC/g). Before use the enzyme preparation was passed through a Sephadex G-25 GPC column to remove any low molecular weight compounds which might interfere with the determination of the reducing sugars. 20 mg of NDF was weighed into a tube and 9.6 ml of Sorensen phosphate buffer, pH 7, was added. After a 15-hour incubation at room temperature the enzyme (0.4 ml) was added and the initial rate of sugar release determined. A one-ml sample was withdrawn at 0, 1, 2.5 and 5 hours. Each sample was mixed immediately with 4 ml of the dinitrosalisylic acid (DNS) reagent used for the analysis of reducing sugars. This reagent interrupts instantly the enzymatic reaction.

Samples were then heated in to boiling water bath for 5 minutes, rapidly cooled in an ice bath and the absorbance was measured at 540 nm. The results were expressed as moles of reducing sugars released per hour per gram of NDF.

Quantification of the reducing ends in NDF was assayed with a modified DNS assay. 20 mg of NDF was weighed into a tube, 1 ml of water added, the mixture was incubated for one hour at room temperature, 4 ml of the DNS reagent was added, the mixture was heated in a boiling water bath for 5 min, cooled rapidly in an ice bath, filtered, and the absorbance of the filtrate was measured at 540 nm. The results were expressed as moles per gram of NDF.

The number of reactive hydroxyl groups was determined by analyzing the number of acetyl groups incorporated in the following acetylation procedure. Triplicate 20 mg NDF samples were mixed with 2 ml of pyridine. 200 µl of $^{14}$C-acetic acid anhydride (specific activity $1.04 \times 10^9$ dpm/mol) was added and the mixture was incubated in sealed vials at 70° C. for 30 min. The filtrate was removed and the precipitate was washed twice with 4 ml of fresh pyridine and then 4 times with water using an ultrasound bath to intensify the washout of the noncovalently bound acetate from the fiber. The last washing solution was analyzed for radioactivity and did not exceed the background level. Acetylated fiber was hydrolyzed with 2 ml of 4N HCl at 90° C. for 5 hours and finally the radioactivity was measured from the neutralized filtrate. Acetyl incorporation was expressed as µmols per gram of NDF.

The results obtained are summarized in table 3.

TABLE 3

Effects on enzyme fractions, alone and in different combinations, on the fiber structure.

| Enzyme | NDF % DM | Red. end* µmol/g(NDF) | Rate of sugar release* µmol/g(NDF)/h | Acet. inc.* µmol/g(NDF) |
|---|---|---|---|---|
| Zero | 35 | 0 | 0 | 0 |
| ABCD | 18 | −3 | −144 | 17 |
| ABC | 24 | 2 | 45 | −13 |
| ABD | 20 | −3 | −143 | 55 |
| ACD | 20 | −3 | −139 | 17 |
| BCD | 23 | −6 | −140 | 29 |
| AB | 27 | 2 | 58 | −62 |
| AC | 27 | 2 | 92 | −13 |
| AD | 21 | −3 | −121 | 55 |
| BC | 28 | 0 | −49 | −2 |
| BD | 25 | −6 | −138 | 116 |
| CD | 23 | −6 | −141 | 29 |
| A | 30 | 2 | 173 | −62 |
| B | 32 | 0 | −40 | 0 |
| C | 31 | 0 | −53 | −2 |
| D | 26 | −6 | −125 | 116 |

*The reported values are relative to the zero control value.
DM is dry matter

The NDF values decreased when enzymes were used in silage making. The treatment with the enzyme mixture ABCD decreased NDF to 18% from 35% DM obtained with the non-enzyme treated silage. The NDF drop was less when the enzyme fraction D was omitted. Enzyme fraction D had the strongest effect on the NDF solubilization. When D was combined with other fractions, the fiber was very efficiently dissolved. This explains also why the number of reducing ends went down in the presence of D. It is believed that fraction D systematically digests the fiber, thereby solubilizing the mass. The number of free ends decreased to a level lower than that found from the control with no enzyme treatment. Also effective in the solubilization of NDF was fraction A in combinations with fractions B and C. Fraction A also greatly improves the reactivity, possibly by increasing the number of reducing ends.

It is desirable to modify the fiber during ensilage so that it will be easier for the rumen microbes to attack it and make it more reactive in the monogastric tract. The initial attack in the rumen is by the cellulolytic microbes and their enzymes. The initial rate of enzymatic sugar release was therefore determined as a measure of the susceptibility of NDF fractions to said attack. The values are compared to the no enzyme control (zero) with positive values indicating an increase in the availability of sugar for rumen microbes and negative values showing that too much sugar has been converted to acids in the ensilage process. It can be seen that enzyme fraction D, alone or in combinations, is less suitable for use in the ensilage process due to the strong sugar release efficiency. Fraction A had a strong positive effect on the initial rate of sugar production. 95% of the sugars released consisted of glucose and cellobiose. When both A and D were present, fraction D was the dominating one. Fraction A, alone or in combination with B, C or BC, improves the availability of sugar to the rumen microbes and is beneficial for this application. Acetylation of the NDF fractions from the enzyme treated silages showed that the removal of the carbohydrate component of the cell wall material does not decrease the number of reactive hydroxyl groups. On the contrary, the efficiency of the carbohydrate digesting enzyme combinations increased $^{14}$C-acetyl incorporation onto the treated fiber. The most effectively solubilizing enzyme combinations and the Cytolase itself hence increased the number of exposed hydroxyl groups. Fraction D had the greatest effect on the number of hydroxyl groups. Probably the hydroxyl groups exposed were phenolic-lignin substituents. Fraction C seemed to be an antagonist to D. Again, the effect of A was opposite to that of the fraction D.

On the basis of the invention it is hence possible to modify the nonsoluble part of silage in several ways by selecting different enzyme combinations. The most notable effects are obtained by the use of, or deletion of, where appropriate, fractions A and D, alone or in combinations. Ensiling of forage in the presence of enzyme fraction D in any combination produces an insoluble fraction that cannot be further hydrolyzed enzymatically by the enzyme mixture used. Fraction A has the opposite effect; the silage made with A but without D is clearly more susceptible to further enzymatic hydrolysis than the non-enzyme treated control. Although not all fractions and fraction combinations have been discussed in detail, it is clear that all possible fraction combinations fall within the scope of the present invention.

EXAMPLE 3

EFFECT OF ENZYME FRACTIONS PREPARED FROM CYTOLASE-123 ON PRODUCTION OF EFFLUENT AND CHEMICAL COMPOSITION OF SILAGE MADE WITH TETRAPLOID RYEGRASS

Tetraploid ryegrass (fertilization 120 kg N/hectare) was cut by hand using aseptic techniques, transported cold and the experiment started within 5 hours of cutting. The dry matter content was 13% wt/wt and the pH 6.35. The grass was cut with scissors to 1 cm pieces and placed in plastic bags, each containing 80 g of fresh grass. Replicate samples were treated with several combinations of Cytolase-123 fractions A, B, C and D. After the enzyme treatment the grass was loosely packed in 5 g aliquots into 20 ml anaerobic culture tubes, flushed with anaerobic gas for 5 minutes, packed more tightly and sealed with butyl rubber stoppers. Nine replicates were made for each treatment. The tubes were incubated at 30° C. and replicates opened at 1, 2 and 4 weeks. The whole contents of a tube (5 g) was used as a sample for each analysis.

Effluent determination. The content of one tube (5 g was quantitatively packed into a balanced, perforated plastic tube which was placed inside at 50 ml centrifuge tube having a 2 cm spacer on the bottom. The tubes were centrifuged at 1000 rpm speed in a Sorvall rotor SS-34 for 20 minutes. The perforated inner tubes with the precipitate were balanced again and the amount of effluent was calculated (effluent= 5—weight of the precipitate).

Acid production was analyzed in several different ways. The pH of the silage effluent was measured after 1, 2 and 4 weeks of incubation. Simultaneously the total titrable acids were determined. In this analysis the acids which were in salt form at the pH value (4) of the effluent were excluded. Lactic acid is one of the acids having a pKa value lower than the starting pH of the titration. Lactic acid and acetic acid were separately analyzed by HPLC with a $H^+$ form column and UV detection at 210 nm.

Acid titration. 15 ml of distilled water was added to a tube with 5 grams of silage. The tube was shaken at room temperature for 1 hour, filtered through a 0.2 um filter and divided into three equal parts. Two of the samples were used for analysis of organic acids and one for acid titration. The sample was diluted with distilled water and titrated with 0.05 M NaOH to neutrality using phenolphthalein as an indicator. The results are summarized in Table 4.

TABLE 4

EFFECT OF CYTOLASE AND ENZYME FRACTIONS ON EFFLUENT AND SILAGE COMPOSITION

| Enzyme | Effluent 28 day ml/g | pH- day 7 | pH- day 28 | Lactic -d7 umol/g | Lactic -d28 umol/g | Titre -7d umol/g | Titre -28d umol/g |
|---|---|---|---|---|---|---|---|
| Zero | 0.45 | 4.04 | 4.02 | 145 | 171 | 107 | 135 |
| ABCD | 0.65 | 3.96 | 3.95 | 164 | 196 | 138 | 173 |
| ABC | 0.53 | 4.15 | 4.06 | 148 | 175 | 117 | 147 |
| ABD | 0.63 | 3.99 | 3.91 | 184 | 223 | 138 | 173 |
| ACD | 0.61 | 4.05 | 3.96 | 171 | 206 | 123 | 154 |
| BCD | 0.56 | 4.12 | 4.04 | 155 | 184 | 116 | 146 |
| AB | 0.52 | 4.11 | 4.03 | 156 | 186 | 117 | 147 |
| AC | 0.49 | 4.17 | 4.08 | 154 | 183 | 104 | 131 |
| AD | 0.59 | 4.08 | 4 | 176 | 206 | 123 | 154 |
| BC | 0.46 | 4.11 | 4.03 | 155 | 184 | 113 | 141 |
| BD | 0.55 | 4.09 | 4 | 159 | 190 | 116 | 146 |
| CD | 0.56 | 4.09 | 4 | 139 | 193 | 111 | 139 |
| A | 0.48 | 4.2 | 4.12 | 150 | 177 | 104 | 131 |
| B | 0.45 | 4.08 | 3.99 | 151 | 179 | 113 | 141 |
| C | 0.46 | 4.07 | 3.99 | 161 | 193 | 107 | 135 |
| D | 0.54 | 4.12 | 4.04 | 153 | 181 | 111 | 139 |

*Values are on a fresh weight basis

From the above results, it is evident that the silages were well preserved, having a pH value of about 4 or lower and a high concentration of lactic acid.

The effluent production from wet crops is a function of enzyme fractions A and D, the latter being especially effective. Enzyme fraction D is responsible for the adverse pattern of effulent flow, with fraction A effluent ceases to flow after about 14 days, but with fraction D it continues during the whole ensilage period.

EXAMPLE 4

It is believed that compositions similar to combinations ABC, ACD, AC and ABD, as well as other combinations, can be prepared by genetic manipulation of the cellulase source. For example, the gene coding for cellobiohydrolase I, cellobiohydrolase II, endoglucanase I, and combinations of the genes coding for these enzymes can be deleted from a Trichoderma species. It is anticipated that the cellulase isolated from such a gene deficient species would have an effect on crops similar to the corresponding combinations of cellulase material fractions from an anion exchange column.

It is also believed that combinations of purified, or enriched, enzymes present in cellulase material would also have an effect on crops similar to corresponding combinations of cellulase material fractioned on an ion exchange column.

What we claim is:

1. A method of treating crops for improving at least one of feed utilization and preservation of said crops, comprising adding to said crops a composition comprising an active enzyme component consisting essentially of a cellulase material, wherein about 99 percent of said cellulase material binds to an anion exchange resin at a pH of about 8 and a conductivity approximately equivalent to that of a 20 mM tris-buffer.

2. A method of treating crops according to claim 1 wherein at least about 99 percent of said cellulase material binds to the anion exchange resin at a pH of about 8 and a conductivity approximately equivalent to that of a 20 mM tris buffer containing 0.08 M NaCl.

3. A method of treating crops according to claim 1 wherein at least about 99 percent of said cellulase material binds to an anion exchange resin at a pH of about 8 and a conductivity approximately equivalent to that of a 20 mM tris buffer containing 0.15 M NaCl.

4. A method of treating crops according to claim 1 wherein at least about 99 percent of said cellulase material (i) binds to an anion exchange resin at a pH of about 8 and a conductivity approximately equivalent to that of a 20 mM tris buffer containing 0.08 M NaCl, and (ii) elutes from said anion exchange resin a conductivity approximately equivalent to that of a 20 mM tris buffer containing 0.15 M NaCl.

5. A method of treating crops according to claim 1 wherein at least about 99 percent of said cellulase material (i) binds to an anion exchange resin at a pH of about 8 and the conductivity of an about 20 mM tris buffer, and (ii) elutes from said anion exchange resin a conductivity approximately equivalent to that of a 20 mM tris buffer containing 0.15 M NaCl.

6. A method of treating crops according to claim 1 wherein at least about 99 percent of said cellulase material (i) binds to an anion exchange resin at a pH of about 8 and the conductivity of an about 20 mM tris buffer, and (ii) elutes from said anion exchange resin a conductivity approximately equivalent to that of a 20 mM tris buffer containing 0.08 M NaCl.

7. A method of treating crops according to claim 1 wherein at least about 99 percent of said cellulase material (i) binds to an anion exchange resin at a pH of about 8 and the conductivity of an about 20 mM tris buffer, and (ii) elutes from said anion exchange resin a conductivity approximately equivalent to that of a 20 mM tris buffer containing between about 0.01 and 0.08 M NaCl, and a conductivity approximately equivalent to that of a 20 mM tris buffer containing greater than about 0.15 M NaCl.

8. A method of treating crops according to claim 1 wherein said solution of cellulase material is added to standing crops.

9. A method of treating crops according to claim 1 wherein said solution of cellulase material is added to harvested crops.

10. A method of treating crops according to claim 1 wherein said solution of cellulase material is added to harvested crops within about 48 hours before feeding said crops to an animal.

11. The method of claim 1, wherein the cellulase composition is produced by a genetically modified microorganism.

12. The method of claim 11, wherein the microorganism is a Trichoderma species.

13. A method of treating crops for improving at least one of feed utilization and preservation of said crops, comprising adding to said crops a composition including a cellulase material wherein at least about 95% of said cellulase material is a cellulase material that (I) does not bind to an anion exchange resin at a pH of about 8 and a conductivity approximately equivalent to that of a 20 mM tris buffer, (ii) binds to said resin at a pH of about 8 and a conductivity approximately equivalent to that of 20 mM tris buffer containing 0.08 M NaCl, or (iii) is a combination of (I) and (ii).

14. A method of treating crops according to claim 13 wherein at least about 95 percent of said cellulase material is cellulase material that (i) does not bind to an anion exchange resin at a pH of about 8 and a conductivity approximately equivalent to that of a 20 mM tris-buffer, (ii) binds to said resin at a pH of about 8 and a conductivity approximately equivalent to that of a 20 mM tris buffer containing 0.15 M NaCl, or (iii) is a combination of (i) and (ii).

15. A method of treating crops according to claim 13 wherein at least about 95 percent of said cellulase material does not bind to an anion exchange resin at a pH of about 8 and a conductivity approximately equivalent to that of a 20 mM tris-buffer.

16. A method of treating crops according to claim 13 wherein at least about 95 percent of said cellulase material is cellulase material that (i) does not bind to an anion exchange resin at a pH of about 8 and a conductivity approximately equivalent to that of a 20 mM tris-buffer, (ii) binds to said resin at a pH of about 8 and a conductivity approximately equivalent to that of a 20 mM tris buffer containing between about 0.08 and about 0.15 M NaCl, or (iii) is a combination of (i) and (ii).

17. A method of treating crops for improving at least one of feed utilization and preservation of said crops, comprising adding to said crops a composition a cellulase material and at least about 95% of said cellulase material is cellulase material that (i) does not bind to an anion exchange resin at a pH of about 8 and a conductivity approximately equal to that of 20 mM tris buffer containing about 0.08 M NaCl, (ii) binds to said resin at a pH of about 8 and a conductivity approximately equivalent that of 20 mM tris buffer containing about 0.15 M NaCl, or (iii) is a combination of (I) and (iii).

18. A method of treating crops according to claim 17 wherein at least at least about 95 percent of said cellulase material does not bind to an anion exchange resin at a pH of about 8 and a conductivity approximately equivalent to that of a 20 mM tris buffer containing about 0.08 M NaCl.

19. A method of treating crops comprising adding to said crops a solution of a cellulase material, at least about 95 percent of said cellulase material does not bind to an anion exchange resin at a pH of about 8 and a conductivity approximately equivalent to that of a 20 mM tris buffer containing 0.15 M NaCl.

* * * * *